United States Patent [19]

Yoshimoto et al.

[11] 3,969,102
[45] July 13, 1976

[54] HERBICIDES

[75] Inventors: Takeo Yoshimoto; Keiichi Igarashi, both of Yokohama; Takeo Harayama, Kamakura; Masaaki Ura, Kamakura; Naoki Sato, Kamakura; Teruhiko Toyama, Fujisawa; Osamu Morikawa; Yoshio Takasawa, both of Chigasaki; Taisuke Kurechi, Yokohama, all of Japan

[73] Assignee: Mitsui Toatsu Chemicals, Incorporated, Tokyo, Japan

[22] Filed: Aug. 21, 1974

[21] Appl. No.: 499,284

[30] Foreign Application Priority Data
Aug. 28, 1973 Japan.............................. 48-95712

[52] U.S. Cl.............................. 71/124; 260/613 R
[51] Int. Cl.$^2$..................... A01N 9/24; C07C 43/20
[58] Field of Search................... 260/613 R; 71/124

[56] References Cited
UNITED STATES PATENTS

| | | | |
|---|---|---|---|
| 2,676,880 | 4/1954 | Schlesinger | 71/124 |
| 2,988,571 | 6/1961 | MacFie et al. | 260/613 R |
| 3,294,847 | 12/1966 | Albright et al. | 260/613 R X |
| 3,376,281 | 4/1968 | Cox et al. | 260/613 D X |
| 3,776,961 | 12/1973 | Theissen | 260/613 R |
| 3,798,276 | 3/1974 | Bayer et al. | 260/613 R |
| 3,849,503 | 11/1974 | Shigehara et al. | 260/613 R |
| 3,928,416 | 12/1975 | Bayer et al. | 260/613 R |

FOREIGN PATENTS OR APPLICATIONS

| | | | |
|---|---|---|---|
| 4,634,633 | 11/1971 | Japan | 71/124 |

*Primary Examiner*—James O. Thomas, Jr.
*Assistant Examiner*—G. Breitenstein
*Attorney, Agent, or Firm*—Lane, Aitken, Dunner & Ziems

[57] ABSTRACT

2,4-Dichloro-3'-($\beta$-chloroethoxy)-4'-nitrodiphenyl ether is prepared by condensing 2,3',4-trichloro-4'-nitrodiphenyl ether with ethyleneglycol in the presence of an acid-binding agent and then chlorinating the hydroxyethoxy group of the resulting condensate. This compound posesses an excellent herbicidal activity to a wide variety of undesirable weeds with an extremely low phyto-toxicity to useful crops.

5 Claims, No Drawings

HERBICIDES

BACKGROUND OF THE INVENTION

This invention relates to a new compound possessing excellent herbicidal activity, a process for preparing same and a herbicide comprising the new compound.

Many diphenylether compounds have previously been examined to determine their effects in practical use as herbicides. In many cases, the presence or absence, degree, mode of action, selectivity and persistence of the herbicidal activities of these compounds differ with even a slight difference in chemical structure of these compounds such as type, number and position of substituents. Thus, it is extremely difficult to estimate the herbicidal activity of these compounds from their similarity in chemical structure.

It is a well-known fact that some diphenylether compounds possess excellent herbicidal activity. For example, 2,4-dichloro-4'-nitrodiphenyl ether (referred to hereinafter as NIP) and 2,4,6-trichloro-4'-nitrodiphenyl ether (referred to hereinafter as CNP) are widely used as herbicides in rice fields.

Ideal herbicides are required to exhibit on one hand a very strong herbicidal activity to undesirable plants even at a very low level concentration and on the other hand an extremely low phyto-toxicity to useful plants. However, known herbicides still fail to meet fully either or both of these requirements. In recent years, the problem of environmental pollution has been raised in connection with the use of agricultural chemicals and the use of a highly effective herbicide in an amount as small as possible is recommended to minimize any environmental effect. Under these circumstances, there is a great demand for a new type of herbicide which meets the aforementioned requirements.

BRIEF SUMMARY OF THE INVENTION

It is therefore an object of this invention to provide a new diphenylether compound possessing a very strong herbicidal activity even at a low level concentration.

It is another object of this invention to provide a process for the production of the new diphenylether compound.

It is still another object of this invention to provide a herbicide comprising the new compound as active ingredient.

It is further an object of this invention to provide a method for controlling weeds by applying the herbicide thereto.

Other and further objects, features and advantages of this invention will become more apparent from the following description.

DETAILED DESCRIPTION OF THE INVENTION

It has now been found that 2,4-dichloro-3'-($\beta$-chloroethoxy)-4'-nitrodiphenyl ether exhibits an excellent herbicidal activity as compared with NIP and CNP.

In accordance with this invention, there is provided a new herbicidally active 2,4-dichloro-3'-($\beta$-chloroethoxy)-4'-nitrodiphenyl ether represented by the formula:

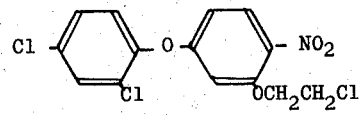

The above new compound of this invention is a light yellow crystalline substance and may be purified by recrystallization from an organic solvent such as a lower alcohol.

In accordance with another embodiment of this invention, there is provided a process for the preparation of 2,4-dichloro-3'-($\beta$-chloroethoxy)-4'-nitrodiphenyl ether. According to the process of this invention, this new compound is prepared by a simple two-step reaction which comprises first condensing 2,4',4-trichloro-4'-nitrodiphenyl ether with ethylene glycol in the presence of an acid-binding agent and then chlorinating the hydroxyethoxy group of the resulting 2,4-dichloro-3'-($\beta$-hydroxyethoxy)-4'-nitrodiphenyl ether. A series of these reactions are known and can be carried out in any manner conventionally adopted for hydroxyalkylation of halogen atoms and halogenation of $\beta$-hydroxyalkoxy groups. For example, the condensation reaction in the first step is carried out by reacting 2,4',4-trichloro-4'-nitrodiphenyl ether with ethylene glycol at an elevated temperature in the presence of a suitable acid-binding agent and optionally, with a liquid vehicle. Examples of suitable acid-binding agents are caustic alkalis such as potassium hydroxide and sodium hydroxide, alkali metal carbonates such as sodium carbonate and sodium bicarbonate, and tertiary amines such as triethylamine and pyridine. Preferred examples of the liquid vehicle include water, lower alcohols and mixtures thereof. The reaction is preferably carried out at an elevated temperature up to the reflux temperature of the mixture. Chlorination of the hydroxyethyl group in the resulting 2,4-dichloro-3'-($\beta$-hydroxyethoxy)-4'-nitrodiphenyl ether is carried out by warming this intermediately formed condensate with an adequate chlorinating agent such as thionyl chloride or dry hydrogen chloride in a suitable solvent. The use of thionyl chloride is preferred because of its ease in handling and reactivity. The end product is purified by recrystallization from an alcohol but may be used directly as active ingredient for the herbicide.

In accordance with still another example of this invention, there is provided a herbicide comprising 2,4-dichloro-3'-($\beta$-chloroethoxy)-4'-diphenyl ether as active ingredient.

The new compound may be used without a vehicle or carrier as a herbicide, but in general, it is dissolved in or dispersed into an appropriate liquid vehicle (such as an organic solvent) or alternatively mixed with or adsorbed with an appropriate inert solid carrier (such as a diluent or weighting agent). The herbicide may be used in various forms such as an emulsifiable concentrate, wettable powder, granule dust etc., if necessary by mixing the herbicide with an adjuvant such as an emulsifier, stabilizer, dispersing agent, suspending agent, vehicle, wetting agent or permeating agent. Preferred examples of the liquid vehicle include alcohols, naphtha, and aliphatic and aromatic hydrocarbons while preferred examples of the inert solid carrier include mineral powders such as talc, bentonite, etc. and insoluble inorganic compounds such as calucium carbonate, silica, etc.

The herbicide of this invention may be used in combination with one or more other agricultural chemicals including other herbicides, insecticides, fungicides and plant growth regulators, soil conditioners and fertilizers. It is also possible to manufacture preparations containing the herbicide of this invention in combination with these agricultural chemicals. Examples of other herbicides which may be combined with the herbicide of this invention include those of the urea series, thiolcarbamate series and acid amide series.

The concentration of the active ingredient in the herbicide of this invention is preferably 1 – 10% in the case of granules, 20 – 80% in the case of wettable powder and 10 – 50% in the case of emulisifiable concentrate (all the percentages are by weight).

In comparison with NIP or CNP, the active ingredient of this invention exhibits excellent herbicidal activity to barnyard grass and other kinds of weeds. Its activity is scarcely weakened when the active ingredient is diluted to a low concentration. In addition, the active ingredient of this invention exhibits prolonged herbicidal activity and little damage to useful crops.

In another respect of this invention, there is provided a method of controlling growth of plants which comprises applying the herbicide to undesirable plants or the soil containing them.

In a post-emergence treatment for killing weeds, the herbicide, preferably in the form of an emulsion, is applied, in an amount sufficient to inhibit growth of the weeds, over the entire field by any suitable means such as sprinkling. In a pre-emergent treatment where the herbicidal effect is maximally exhibited, the herbicide in any desired form such as a wettable powder or granular preparation is blended with soil containing the weed seeds. In the case of pre-emergence treatment, germination of weeds is almost entirely inhibited and the herbicidal effect is maintained for a prolonged period of time.

This invention will now be explained in more detail by way of Examples.

Example 1 Preparation of the active ingredient

In a 300 ml four-necked flask equipped with a stirrer, a thermometer, a condenser and an inlet for starting materials were placed 100 ml of ethylene glycol and 4.2 g of potassium hydroxide (85% solid) (0.064 mole). The mixture was warmed to dissolve the potassium hydroxide in the ethylene glycol. The solution was cooled to 20°C, and 20 g of finely pulverized 2,3′,4-trichloro-4′-nitrodiphenyl ether (0.063 mole) were added at once to the solution with agitation. The temperature of the flask contents was maintained at 90°C by external heating and the reaction was continued for 6 hours. The reaction mixture was cooled to room temperature and poured into 200 ml of water whereby an oily substance was precipitated which was then extracted with 300 ml of benzene. The benzene phase was washed with 200 ml of a 5% aqueous solution of sodium hydroxide and then with water thoroughly until the aqueous phase became neutral. The benzene phase was allowed to stand and then separated. After dehydration of the benzene phase with anhydrous sodium sulfate, benzene was removed by evaporation under reduced pressure leaving 16 g of a viscous oily substance. The oily substance was composed predominantly of 2,4-dichloro-3′-($\beta$-hydroxyethoxy)-4′-nitrodiphenyl ether.

The oily substance was dissolved in 100 ml of benzene and was placed in a 300 ml four-necked flask equipped with a stirrer, a thermometer, an inlet for starting materials and a condenser with a gas-absorbing apparatus at one end thereof. The interior temperature was maintained at 60°C and 15 g of thionyl chloride were added dropwise over about 30 minutes to the mixture with agitation. The reaction was continued for 4 hours with agitation at the same temperature. After transfer of the reaction mixture to an evaporation flask, benzene and excess thionyl chloride were removed by evaporation under reduced pressure whereupon 16 g of a crystalline residue were obtained. The crystalline residue was dissolved in a tenfold volume of ethanol by warming and then cooled to 10°C to effect recrystallization whereby 9 g of 2,4-dichloro-3′-($\beta$-chloroethoxy)-4′-nitrodiphenyl ether were obtained in the form of light yellow crystals (m.p. 104° – 105.5°C). Elementary analysis gave $C_{14}H_{10}Cl_3NO_4$

|  | C (%) | H (%) | N (%) | Cl (%) |
|---|---|---|---|---|
| calc. | 46.37 | 2.78 | 3.86 | 29.34 |
| found | 46.66 | 2.76 | 3.97 | 29.20 |

Example 2 Granular preparations

5 Parts of the active ingredient obtained in Example 1, 70 parts of bentonite, 20 parts of talc, 3 parts of sodium dodecylbenzenesulfonate and 2 parts of sodium ligninesulfonate were mixed and kneaded with an appropriate amount of water. The mixture was shaped into granules by a conventional method using a pelletizer whereby 100 parts of a granular preparation were obtained.

Example 3 Wettable powder

50 Parts of the active ingredient, 40 parts of talc, 7 parts of sodium laurylsulfate, and 3 parts of sodium alkylnaphthalenesulfonate were mixed to prepare 100 parts of a wettable agent.

Example 4 Emulisifiable concentrate

10 Parts of the active ingredient, 10 parts of Sorpol 800 A (an emulsifier manufactured by Toyo Chemicals, Co., Ltd.) and 80 parts of solvent naphtha were mixed to prepare 100 parts of a stock solution for forming an emulsion. The emulisifiable concentrate was diluted with water to form an emulsion suitable for spraying.

Example 5 Evaluation of herbicidal effect

3 Kg of an air-dried soil (which passed a sieve of 14 mesh) from a rice field containing common rice field weeds living in natural state were placed in a/5000 Wagner pot, to which 0.8 g each of N, $P_2O_5$ and $K_2O$ was evenly added in the form of compound fertilizers.

The soil was mixed with an appropriate amount of water, and the level of water was maintained above that of the soil. There rice seedlings (2.5 leaf stage) which had been grown in a greenhouse were planted in the pot and kept in a greenhouse. The weeds started to sprout five days after the transplantation of rice. Then, a given amount of a compound to be tested was added to the water in the form of granules prepared as described in Example 2.

One month after the treatment, the phytotoxicity to rice plant and the herbicidal effects on weeds were observed and the results tabulated below were obtained. During the test period the depth of water in the pots was at all times maintained at 3 cm.

Scales for herbicidal efficiency were established with "0" assigned for no effect on weeds and "5" complete death of weeds and scales for phytotoxicity were used with "0" for no injury to the rice plant and "5" for severe injury to the rice plant.

| Compounds tested | amount (active ingredient g/a) | rice | barnyard grass (Echinochloa Crus-galli) | other weeds broad-leaved | other weeds narrow-leaved |
|---|---|---|---|---|---|
| active ingredient of this invention | 5 | 0 | 3 | 5 | 5 |
| | 10 | 0 | 5 | 5 | 5 |
| | 20 | 0 | 5 | 5 | 5 | tested was added to the water in the form of an emulsifiable concentrate prepared according to Example 4.

One month after the treatment, the phytotoxicity to rice plant and the herbicidal effects on weeds were observed and the results tabulated below were obtained. The depth of water was maintained at all times at 3 cm during the test period. Herbicidal efficiency and phytotoxicity were evaluated in the same manner as described in Example 5.

| Compounds tested | Amount used (active ingredient g/a) | Rice | Barnyard grass (Echinochloa Crus-galli) | Umbrella sedge (Cyperus difformis) | Monochoria (Monochoria vaginalis) | Bulrush (Scirpus juncoides) | Water plantain (Alisma canaliculatum) | Spike rush (Eleocharis acicularis) |
|---|---|---|---|---|---|---|---|---|
| Active ingredient of this invention | 2 | 0 | 4 | 4 | 4 | 3 | 4 | 3 |
| | 5 | 0 | 5 | 5 | 5 | 5 | 5 | 5 |
| | 10 | 0 | 5 | 5 | 5 | 5 | 5 | 5 |
| (Comparison) NIP | 2 | 1* | 1 | 1 | 2 | 0 | 0 | 1 |
| | 5 | 2* | 2 | 2 | 2 | 1 | 1 | 2 |
| | 10 | 4* | 3 | 4 | 3 | 2 | 2 | 3 |
| (Comparison) CNP | 2 | 1* | 1 | 1 | 1 | 0 | 0 | 1 |
| | 5 | 2* | 2 | 2 | 2 | 1 | 1 | 2 |
| | 10 | 3* | 3 | 3 | 2 | 2 | 2 | 3 |
| Untreated | | 0 | 0 | 0 | 0 | 0 | 0 | 0 |

Note:
*Brownish discoloration of the leaf sheath of the rice plant was caused by the phytotoxicity of the compound.

| (comparison) CNP | 5 | 0 | 1 | 2 | 1 |
| | 10 | 1* | 2 | 3 | 2 |
| | 20 | 3* | 4 | 4 | 4 |
| (comparison) CNP | 5 | 0 | 2 | 3 | 1 |
| | 10 | 1* | 3 | 3 | 3 |
| | 20 | 2* | 4 | 5 | 4 |
| untreated | | 0 | 0 | 0 | 0 |

Note:
*Brownish discoloration of the leaf sheath of the rice was caused by the phytotoxicity of the compound.

Example 6 Evaluation of herbicidal activity

A rice field in which common rice field weeds were growing in naturally mixed state was plowed, fertilized and watered. The surface of the soil was flattened by secondary plowing. The rice field was divided into areas of 1000 cm³. Two seedlings (leaf age 1.3) of rice were taken as a unit of transplantation and 3 units were planted in each area.

On the day following the day of transplantation of rice seedlings, a given amount of a compound to be tested was added to the water in the form of an emulsifiable concentrate prepared according to Example 4.

As is evident from the results of these tests, the herbicide of this invention not only exhibits a very strong herbicidal activity against various undesirable weeds but also has better characteristics than the conventional diphenyl ether herbicides in that a low level concentration is very effective and its phytotoxicity to useful crops is extremely low.

What is claimed is:

1. 2,4-Dichloro-3'-($\beta$-chloroethoxy)-4'-nitrodiphenyl ether.

2. A herbicide comprising 2,4-dichloro-3'-($\beta$-chloroethoxy)-4'-nitrodiphenyl ether in a herbicidally effective amount and an inert carrier or vehicle.

3. A herbicide according to claim 2 wherein said ether in dissolved in or dispersed in a liquid vehicle.

4. A herbicide according to claim 3 wherein said liquid vehicle is solvent naphtha.

5. A herbicide according to claim 2 wherein said inert carrier is a solid selected from mineral powders and insoluble inorganic compounds.

* * * * *